(12) United States Patent
Jullien et al.

(10) Patent No.: US 6,893,546 B2
(45) Date of Patent: May 17, 2005

(54) METHOD FOR SEPARATING A CHEMICAL OR BIOLOGICAL COMPOUND IN A MIXTURE OF SIMILAR COMPOUNDS BY DIFFUSION IN A MEDIUM SUCH AS A GEL

(75) Inventors: Ludovic Jullien, Arcucil (FR); Herve Lemarchand, Villemoisson sur Orge (FR); Annie Lemarchand, Villemoisson sur Orge (FR)

(73) Assignee: Centre National de la Recherche Scientifique, Paris (FR)

( * ) Notice: Subject to any disclaimer, the term of this patent is extended or adjusted under 35 U.S.C. 154(b) by 370 days.

(21) Appl. No.: 10/128,431

(22) Filed: Apr. 24, 2002

(65) Prior Publication Data
US 2003/0036503 A1 Feb. 20, 2003

Related U.S. Application Data

(63) Continuation of application No. PCT/FR00/02974, filed on Oct. 25, 2000.

(30) Foreign Application Priority Data
Oct. 26, 1999 (FR) .............................................. 9 13366

(51) Int. Cl.$^{7}$ .................... G01N 27/447; G01N 33/559; C02F 1/28
(52) U.S. Cl. ....................... 204/457; 204/456; 210/656; 436/515
(58) Field of Search ................................. 204/450, 457, 204/458; 436/514–516; 210/656, 748

(56) References Cited

U.S. PATENT DOCUMENTS

| | | | |
|---|---|---|---|
| 5,059,294 A | 10/1991 | Lizardi | |
| 5,084,157 A | 1/1992 | Clark et al. | |

FOREIGN PATENT DOCUMENTS

| | | | | |
|---|---|---|---|---|
| WO | WO 84/02001 | 5/1984 | .......... | G01N/27/26 |
| WO | WO 99/45374 | 9/1999 | .......... | G01N/27/26 |

Primary Examiner—Alex Noguerola
(74) Attorney, Agent, or Firm—Birch, Stewart, Kolasch & Birch, LLP

(57) ABSTRACT

A method for separating a chemical or biological compound present in a mixture of similar compounds by diffusion in a medium, the method comprising reacting the compounds of the mixture with a component (P) present in the medium to obtain products ($Q_i$), wherein the reactions $C_i+P \rightarrow Q_i$ are reversible and have kinetic constants $k_1$ and $k_2$, and applying to the medium a varying field to which the compounds are sensitive, wherein the period of the field and the concentration of component (P) in the medium are determined from the kinetic constants ($k_1, k_2$) of the compound (C) to be separated in order to establish resonance condition between said reactions and the field and for giving compound C an apparent diffusion coefficient ($D_a$) in the medium that is maximum.

16 Claims, 2 Drawing Sheets

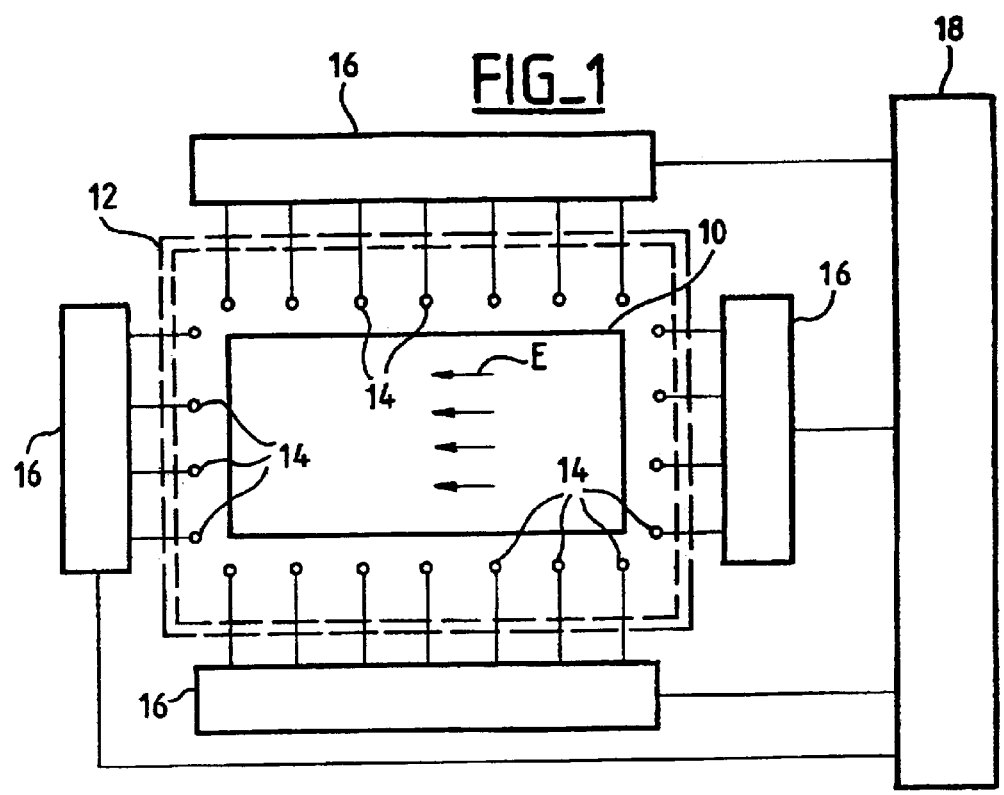
FIG_1
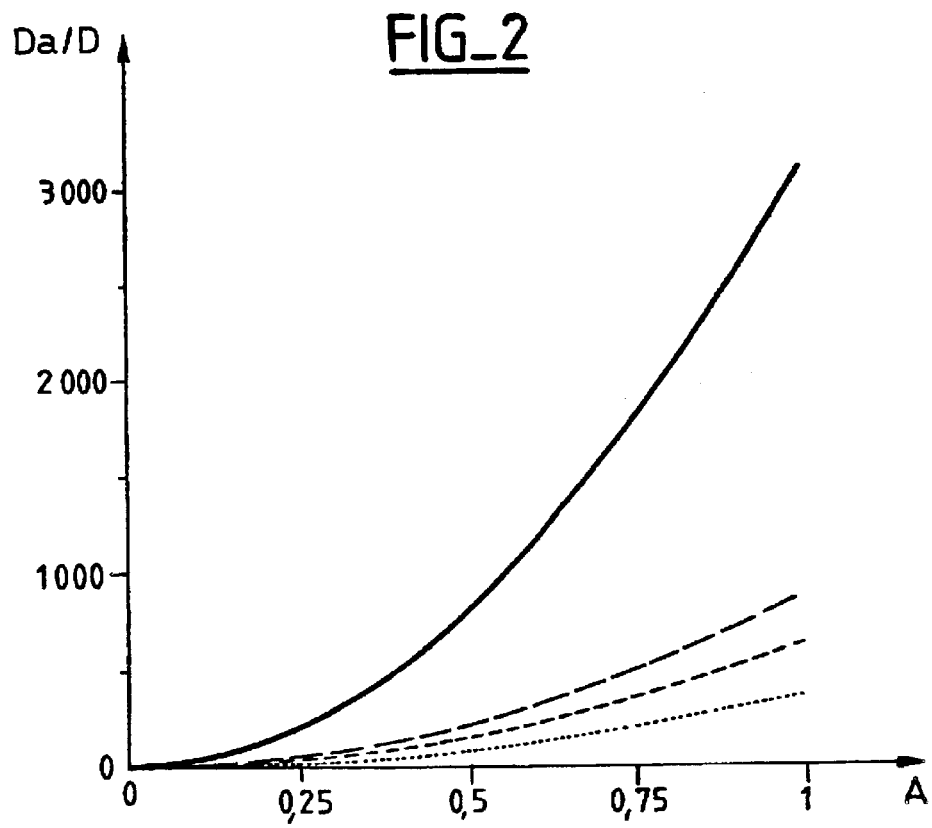
FIG_2

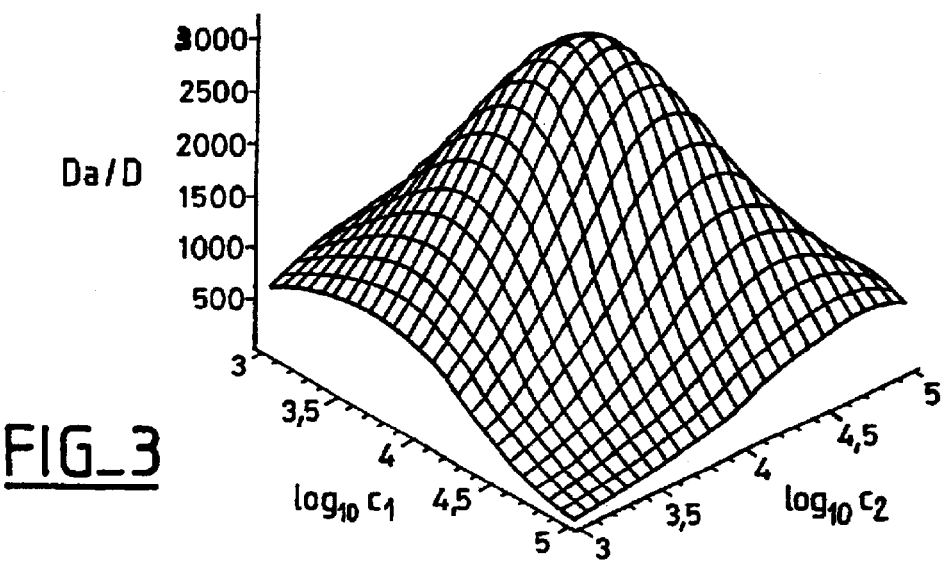
FIG_3
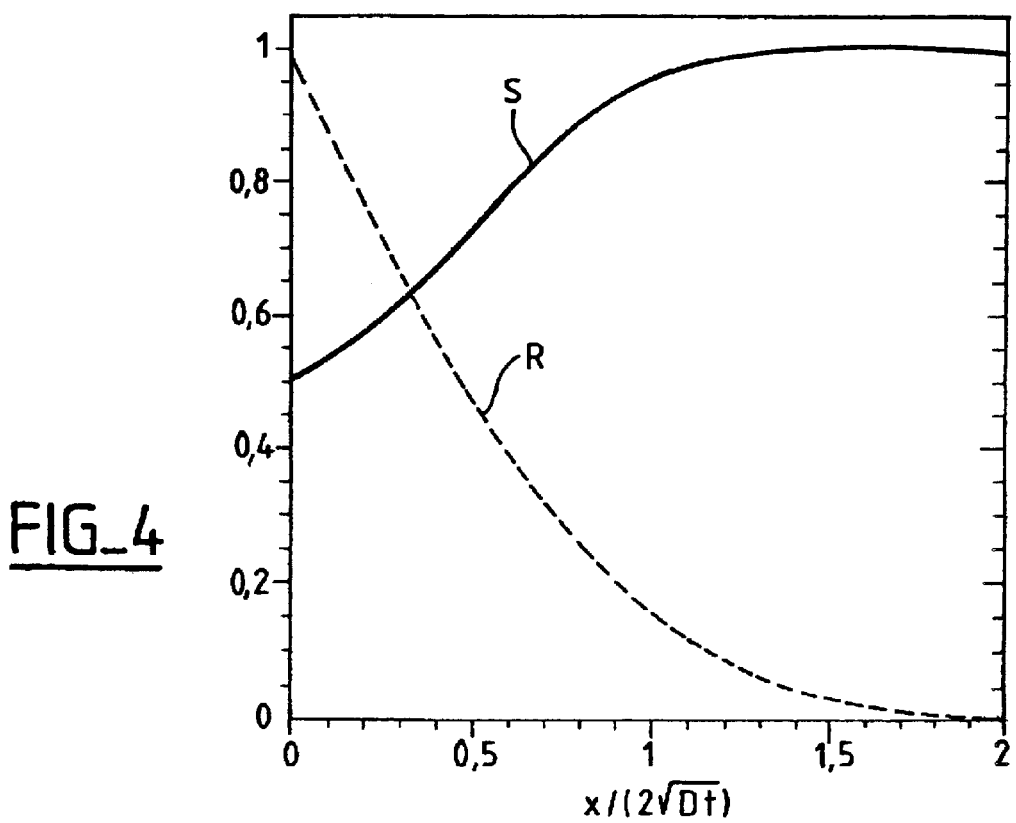
FIG_4

METHOD FOR SEPARATING A CHEMICAL OR BIOLOGICAL COMPOUND IN A MIXTURE OF SIMILAR COMPOUNDS BY DIFFUSION IN A MEDIUM SUCH AS A GEL

This application is a continuation under 35 U.S.C. 120 of PCT/FR00/02974, which was filed on October 25, 2000.

The invention relates to a method for separating a chemical or biological compound present in a mixture of similar compounds by diffusion in a suitable medium such as a gel.

Known methods for separating a compound present in a mixture generally comprise applying a chemical reaction (in its broad sense) and/or a set of external forces to the mixture of compounds. As an example, affinity chromatography can take a mixture of molecules and extract the most strongly retained or the least strongly retained molecules as regards interaction sites bound to a chromatographic support as those molecules occupy privileged positions at the elution head and tail. However, particularly when the mixture contains ten or more similar compounds, it is difficult to isolate compounds with an intermediate affinity, very difficult to isolate compounds with a quantitatively defined affinity, and impossible to separate compounds for which the affinities should be identical but which should have distinct kinetic interaction constants.

The problem with separating compounds present in a mixture and with kinetic interaction constants for a given target that are arbitrarily defined by an operator primarily lies in the field of developing novel therapeutic treatments based on optimising the interaction of molecules with suitably selected targets of biological interest (gene sequences, protein, . . . ), and in the field of combination chemistry, in which test molecules are often obtained in the form of "controlled mixtures" of similar molecules.

The present invention aims to provide a simple, effective and relatively easily implemented solution to this problem.

To this end, the invention proposes a method for separating a chemical or biological compound in a mixture of similar compounds by diffusion in a medium such as a gel, the method comprising a step for introducing a mixture of compounds into the medium, characterized in that it consists of:

reacting the compounds $C_i$ of the mixture in the medium with a component P present in the medium to obtain products $Q_i$, the reactions $C_i + P \rightarrow Q_i$ being reversible and having kinetic constants $k_{1,i}$ in the direction of production of products $Q_i$ and $k_{2,i}$ in the reverse direction; and applying to the medium a field that varies periodically with time and to which compounds $C_i$ are sensitive, the period of the field and the concentration of component P in the medium being determined as a function of the kinetic constants $k_1$, $k_2$ of the compound C to be separated to establish resonance conditions between said reactions and the field, for which compound C has an apparent diffusion coefficient in the medium that is a maximum value.

According to the invention, knowledge of the kinetic reaction constants of a compound C with a target allows determination of a concentration of the target in the medium and the periodicity of the field for which the apparent coefficient of diffusion of the compound will be a maximum and much higher than the apparent diffusion coefficients of other compounds, so that this compound will be cleanly separated from the others by diffusion in the medium.

Even when the compounds present in the mixture behave in substantially the same manner and only differ from each other by the kinetic interaction constants with a previously defined target, the method of the invention can define a target concentration in the medium and a period for the field applied to the medium for which the apparent coefficient of diffusion in the medium of the compound to be separated is a maximum as a result of a stochastic resonance between the reactions and the applied field.

As an example, when one of the kinetic constants of compound C to be separated differs from that of the other compounds of the mixture by one order of magnitude, the other characteristics of the compounds being identical or similar, the apparent diffusion coefficient of compound C in the medium is at least 3.5 times higher than that of the other compounds of the mixture, which not only allows it to be separated from the other compounds by diffusion, but can also extract it from the medium in an advantageous yield and with a relatively high degree of purity.

In a preferred implementation of the invention, the field applied to the medium is an electric field and the method is carried out in a conventional electrophoresis apparatus comprising, for example, a tank filled with electrolyte and in which a plate of a suitable gel is placed along with electrodes disposed in the tank around the gel plate and connected to electrical supply means that can apply to the gel plate an electrical field that is uniform across that space and varies periodically with time.

In a variation, said field is a velocity field in the medium and the method is carried out in a chromatography apparatus, for example an HPLC (high performance liquid chromatography) apparatus in which a homogeneous velocity field of an inert carrier fluid is created in the medium using one or two pumps.

The invention will be better understood and further characteristics, details and advantages thereof will become more clear from the following description, made by way of example and with reference to the accompanying drawings in which:

FIG. 1 is a diagram of means for carrying out the invention in the preferred implementation in which the field applied to the medium is an electrical field;

FIG. 2 is a graph showing variations in the ratio of the apparent and intrinsic diffusion coefficients of a compound C as a function of a parameter A corresponding to the amplitude of the amplitude, under resonance conditions and under different conditions;

FIG. 3 is a graph showing the variation in the ratio of the apparent and intrinsic diffusion coefficients as a function of parameters corresponding to the kinetic reaction constants of the compound;

FIG. 4 is a graph showing variations in the purity and yield in the case of pure diffusion of an equimolar mixture of two compounds with different diffusion coefficients, as a function of a dimensionless parameter.

FIG. 1 is a diagram showing an implementation of the invention in which the method is carried out using an electrophoresis apparatus; reference numeral 10 designates a plate of a medium such as a gel, for example agarose gel, of a type routinely used for electrophoresis.

Gel plate 10 is placed in an electrophoresis tank 12 the outline of which is shown as a dashed line, and in which rows of electrodes 14 are disposed formed, for example, by electrically conducting wires that extend perpendicular to the plane of the drawing.

Electrodes 14 are, for example, disposed around the four sides of gel plate 10 and are connected to electrical supply circuits 16, themselves connected to control means 18 that can optionally be computer controlled.

These supply means 16 and control means 18 allow an electric field to be applied to the gel plate 10, which field varies periodically with time and which is substantially uniform in space, i.e., it is the same at any point on gel plate 10, this electric field being orientated, for example, in the plane of the gel plate, in the direction indicated by arrows E.

This technique is known in electrophoresis and is described in International patent application WO-A-84/02001 and U.S. Pat. No. 5,084,157, reference to which should be made for further details.

The method of the invention differs from known electrophoresis techniques essentially in that electrophoresis resulting from applying a periodic electric field to a mixture of compounds takes place in a reactive medium and in that the electric field varies periodically about a mean zero value.

In accordance with the invention, a medium 10 is used that contains a predetermined concentration of a component P that reacts with the compounds contained in a mixture injected at a point of medium 10, compounds $C_i$ of this mixture reacting with the component P to form products $Q_i$ which themselves decompose into initial products $C_i$ and P as indicated below:

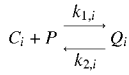

where $k_{1,i}$ and $k_{2,i}$ are the kinetic reaction constants in one direction and in the reverse direction and vary from one compound $C_i$ to another, $k_{1,i}$ being a number of reactions per unit concentration and per unit time, $k_{2,i}$ being a number of reactions per unit time.

The discussion below deals with the most difficult case in which compounds $C_i$ forming the mixture injected into medium 10 are assumed to have the same mass m, the same electric charge z, the same coefficient of friction $\gamma$ in the medium and the same diffusion coefficient D in that medium. Component P present in medium 10 is assumed to be insensitive to the electric field and immobile or capable of diffusing in medium 10 to a small extent, either because it is fixed covalently, or because its dimensions restrict its displacement in medium 10. Compounds $Q_i$ can be mobile to present a response to the action of the field that is distinct from that of compounds $C_i$.

It is also assumed that the concentration of component P is substantially uniform in medium 10 and is kept substantially constant in this medium throughout the separation.

When the electric field applied to medium 10 varies sinusoidally with time, for example in the form $E(t)=a\cos(\omega t)$, the mean value $\overline{X_c}(t)$ and the variance $\sigma_c^2(t)$ in the position x of compound C along an axis parallel to the electric field applied to medium 10 can be calculated. The following formula is obtained:

$$\overline{X_c}(t) = \frac{A}{(c_1+c_2)^2+\omega^2}\left[c_1(1+\cos\omega t) + \frac{c_1c_2+c_2^2+\omega^2}{\omega}\sin\omega t\right]$$

and similarly:

$$\overline{X_Q}(t) = \frac{A}{(c_1+c_2)^2+\omega^2}\left[c_1 + \frac{c_2}{\omega}((c_1+c_2)\sin\omega t - \omega\cos\omega t)\right]$$

where:
$A=za/m\gamma$ is a recalibrated amplitude of the electric field;
$c_1=k_1 p$, p being the concentration of P in medium 10;
$c_2=k_2$;
$c_1$ and $c_2$ being expressed in $s^{-1}$.

While the mean applied electric field is zero, the mean position of compounds $C_i$ and $Q_i$ oscillate about a value other than zero because of the asymmetry of the initial conditions, the system partially retaining a memory of the first excursion of the electric field. Neglecting constant terms and oscillating terms, and for immobile values of P and $Q_i$, after a very short transient state, the variance in position associated with distributions $C_i(x,t)$ and $Q_i(x,t)$ reduce to:

$$\sigma_c^2(t) = \sigma_Q^2(t) = 2D_a t$$

where $$D_a = \frac{c_2}{c_1+c_2}\left[D + A^2\frac{c_1}{2((c_1+c_2)^2+\omega^2)}\right]$$

$D_a$ being the apparent diffusion coefficient of a couple $C_i$, $Q_i$ and D being the intrinsic diffusion coefficient of compound $C_i$.

When the amplitude of the electric field is sufficient for the relationship below to be satisfied:

$$A >> 2D/c_1((c_1+c_2)^2+\omega^2),$$

the apparent diffusion does not depend on D and is controlled solely by the chemical reactions and the electric field, the apparent diffusion coefficient being given by the following relationship:

$$D_a = A^2 \frac{c_1 c_2}{2(c_1+c_2)[(c_1+c_2)^2+\omega^2]}$$

In this case, we have $A=za/m\gamma$ when $Q_i$ are immobile, or $A=za/m\gamma - z_Q a/m_Q \gamma_Q$ where $z_Q$ is the charge carried by $Q_i$, $m_Q$ is the mass of $Q_i$, and $\gamma_Q$ is the coefficient of friction of $Q_i$ when $Q_i$ are immobile.

This apparent diffusion coefficient can take an arbitrarily high value defined by the value of the recalibrated amplitude A of the electric field.

This apparent diffusion coefficient is a function of $c_1$ and $c_2$ and comprises a single maximum (when the amplitude of the electric field is sufficient) which is obtained by:

$$c_1^R = c_2^R = \omega/2$$

or, in an equivalent manner: $k_1^R.p = k_2^R = \pi/T$ where the exponent R expresses a resonance condition and T is the period of the electric field.

In FIG. 2, the solid curve indicates the variation in the ratio $D_a/D$ as a function of A at resonance, the curve in broken lines indicates the variation in this ratio as a function of A for kinetic constants $k_1^R$ and $k_2^R/10$, the curve in short dotted lines indicates the variation in this ratio as a function of A for kinetic constants $10k_1^R$, $10k_2^R$, and the dotted curve indicates the variation of this ratio for kinetic constants equal to $10k_1^R$ and $k_2^R$.

FIG. 3 shows the variation in the ratio $D_a/D$ as a function of the logarithm to the base 10 of $c_1$ and $c_2$, the maximum in the variation corresponding to the resonance conditions cited above.

If the chemical reactions are considered to be random events, transitions between $C_i$ and $Q_i$ are stochastic events and the maximum value of $D_a$ is obtained for conditions that correspond to a stochastic resonance between the chemical reactions and the electric field applied to medium 10.

It is this resonance, which results in a maximum value of the apparent coefficient of diffusion of a compound C, which enables this compound C to be separated from the other components $C_i$ present in the mixture. In particular, it is possible to calculate that, if one of the kinetic constants of a compound $C_i$ is equal to the kinetic constant of a compound C for which there is a resonance and the other kinetic constant of compound $C_i$ differs by a factor of 10 from the other kinetic constant of compound C, the apparent coefficient of diffusion of compound $C_i$ will be about 3.5 times smaller than that of component C.

This difference in diffusion can separate compound C from similar components $C_i$, even when the latter have substantially the same electric charge, the same mass and the same coefficient of friction as C, or substantially the same ratio z/mγ as C (the value of A being substantially the same for all these components) and differ from each other by at least the value of the kinetic reaction constant with component (P).

The electric field applied to medium 10 can vary periodically with time in any manner: the variation can be sinusoidal, a square wave, or any other.

The greatest diffusion of compound C corresponding to the resonance conditions allows it to be separated from other compounds Ci of the mixture and recovered, in part, from the ends of the distribution profile in medium 10. In the case of pure diffusion of a mixture of two compounds ($C_1$, $C_2$) with the same concentration and different intrinsic diffusion coefficients, it is possible to calculate a purity and yield for recovering compound $C_1$ using the following formulae:

$$\text{Purity}: S(\alpha_1) = \frac{I(\alpha_1)}{I(\alpha_1) + I(\alpha_2)}$$

$$\text{Yield}: R(\alpha_1) = \frac{2I(\alpha_1)}{N}$$

Where: N is the quantity of compound $C_1$ injected into medium 10 at time t=0 at point x=0;

I is the integral of the concentration $C_1(x,t)$ between x and infinity;

$$\alpha_1 = \frac{x}{2\sqrt{D_1 t}}$$

and $$\alpha_2 = \frac{x}{2\sqrt{D_2 t}}$$

FIG. 4 shows the variation in purity S and yield R as a function of α. This figure shows that selecting a desired purity enables the value of α and thus that of x to be determined from which it is possible to harvest the compound C, and the yield that will be obtained. When the diffusion coefficients of the two compounds $C_1$ and $C_2$ differ in a ratio of 3.5, 25% of compound $C_1$ can be recovered with a purity of 90%, for $\alpha_1$=0.85.

We shall now describe a brief example of an application of the invention, for clarification. This example concerns the chemical hybridisation of DNA samples to RNA in solution. In the case of samples of oligodeoxyribonucleotides on an RNA target comprising a primary binding site for HIV-1 reverse transcriptase, the binding process is characterized by the following values:

$3 \times 10^4 \, M^{-1}s^{-1} \leq k_1 \leq 10^6 \, M^{-1}s^{-1}$ $10^{-3} \, s^{-1} \leq k_2 \leq 2.5 \times 10^{-2} \, s^{-1}$ $D = 3 \times 10^{-10} \, m^2 s^{-1}$ $2.7 \times 10^{-18} \, C \leq z \leq 5.9 \times 10^{-18} \, C$.

The first resonance condition $k_1.p=k_2$ gives concentrations of RNA in medium 10 in the range $10^{-9}$ M to $10^{-6}$ M, which can be produced without difficulty.

The second resonance condition $\omega=2k_2$ results in a ω in the range $2 \times 10^{-10} \, s^{-1}$ to $5 \times 10^{-2} \, s^{-1}$ and is readily satisfied.

The last condition relating to the amplitude of the electric field is satisfied when this amplitude is much higher than $4 \times 10^{-5} \, V\mu m^{-1}$, which poses no technical problems.

By agreeing the values of ω and p with the values of $k_1$ and $k_2$ in a given sample, it is possible to separate this sample from the others by placing it under stochastic resonance conditions between the RNA fixing reaction and the electric field.

In a further particularly advantageous aspect of the invention, it is also possible to use a non electric field capable of acting on compounds independently of their electric charge. As an example, an HPLC type chromatographic apparatus can be used to this end in which one or two pumps create in the medium a homogeneous velocity field which is caused to vary periodically with time, these velocities possibly being comparable with the rates of displacement obtained by applying an electric field. The magnitude A mentioned in the description above is the value of the velocity created in the medium by the pump.

Further, it is not necessary for component P and products $Q_i$ to remain immobile in the medium subjected to the periodic field; it suffices for products $Q_i$ to respond to the application of this field in a manner different from that of components $C_i$.

In general, the method of the invention is applicable to separating relatively small to large molecules (varying from about 10 to $10^6$ Daltons), proteins, oligonucleotides, oligosaccharides, this separation resulting from combination in the medium of a chemical reaction and any uniform field with a periodic variation with time.

What is claimed is:

1. A method for separating a chemical or biological compound present in a mixture of similar compounds by diffusion in a medium, the method comprising (i) introducing a mixture of compounds into said medium, (ii) reacting the compounds ($C_i$) of the mixture in the medium with a component (P) present in the medium to obtain products ($Q_i$), wherein the reactions $C_i + P \rightarrow Q_i$ are reversible and have kinetic constants $k_{1,i}$ in the direction of production of products ($Q_i$) and ($k_{2,i}$) in the reverse direction; and (iii) applying to the medium a field that varies periodically with time and to which compounds ($C_i$) are sensitive, wherein the amplitude and the period of the field and the concentration of component (P) in the medium are determined from the intrinsic diffusion coefficient and from the kinetic constants ($k_1$, $k_2$) of the compound (C) to be separated in order to establish resonance conditions between said reactions and the field, compound C having an apparent diffusion coefficient ($D_a$) in the medium that is a maximum value at the resonance conditions.

2. The method of claim 1, wherein the amplitude of the field is higher than a limiting value that is calculated from said kinetic constants and from the intrinsic diffusion coefficient of compound (C).

3. The method of claim 1, wherein said compounds ($C_i$) in said the mixture differ from each other at least in the value of one kinetic constant for reaction with component (P).

4. The method of claim 3, wherein one of said kinetic constants of compound (C) to be separated differs from those of the other compounds in the mixture by at least one order of magnitude.

5. The method of claim 1, wherein the period of the field is substantially equal to $\pi/k_2$ and the concentration of component (P) in the medium is substantially equal to $k_2/k_1$.

6. The method of claim 1, wherein the concentration of component (P) in said medium is kept constant during separation.

7. The method of claim 1, wherein said field has an amplitude which varies about a zero mean value.

8. The method of claim 1, wherein said field is substantially uniform in the medium.

9. The method of claim 1, wherein said field is an electric field.

10. The method of claim 1, wherein said field is a velocity field in the medium.

11. The method of claim 1, wherein said component (P) and products ($Q_i$) remain substantially immobile in the medium whether subjected to said field.

12. The method of claim 1, wherein said products ($Q_i$) respond to the field applied to the medium in a manner that is different from that of compounds ($C_i$).

13. The method of claim 1, wherein said compounds to be separated are molecules with a size in the range about 10 to $10^6$ Daltons.

14. The method of claim 1, wherein said compounds to be separated are proteins, oligonucleotides or oligosaccharides.

15. The method of claim 1, wherein said medium is a gel.

16. The method of claim 1, wherein said compounds to be separated have identical characteristics and only differ from each other by the kinetic interaction constants with a previously defined target.

* * * * *